US012773106B2

(12) United States Patent
Jeon et al.

(10) Patent No.: US 12,773,106 B2
(45) **Date of Patent: *Oct. 27, 2026**

(54) INTRAORAL SCANNER

(71) Applicant: ARCREAL INC., Seoul (KR)

(72) Inventors: Seung Hyun Jeon, Seoul (KR); Kyong Kook Kim, Seoul (KR)

(73) Assignee: ARCREAL INC., Seoul (KR)

( * ) Notice: Subject to any disclaimer, the term of this patent is extended or adjusted under 35 U.S.C. 154(b) by 70 days.

This patent is subject to a terminal disclaimer.

(21) Appl. No.: 18/717,739

(22) PCT Filed: Dec. 15, 2022

(86) PCT No.: PCT/KR2022/020456

§ 371 (c)(1),
(2) Date: Jun. 7, 2024

(87) PCT Pub. No.: WO2023/113499

PCT Pub. Date: Jun. 22, 2023

(65) Prior Publication Data

US 2025/0049312 A1 Feb. 13, 2025

(30) Foreign Application Priority Data

Dec. 15, 2021 (KR) ........................ 10-2021-0179478

(51) Int. Cl.
*A61B 1/24* (2006.01)
*A61B 1/06* (2006.01)

(52) U.S. Cl.
CPC .............. *A61B 1/24* (2013.01); *A61B 1/0623* (2013.01)

(58) Field of Classification Search
CPC ..... A61B 1/24; A61B 1/0623; A61B 1/00177; A61B 1/00096; A61B 1/00172;
(Continued)

(56) References Cited

U.S. PATENT DOCUMENTS 8,331,528 B2 * 12/2012 Kayzerman .......... A61B 6/4233 378/38
2011/0141252 A1 * 6/2011 Schmidt ................. H04N 7/183 382/128
(Continued)

FOREIGN PATENT DOCUMENTS

JP H 8-248328 A 9/1996
JP 2000-227332 A 8/2000
(Continued)

OTHER PUBLICATIONS

Notice of Allowance issued on Aug. 25, 2025 from Korean Patent Office in a counterpart Korean Patent Application No. 10-2024-0037235 (English translation is also submitted herewith.).
(Continued)

*Primary Examiner* — Gims S Philippe
(74) *Attorney, Agent, or Firm* — The PL Law Group, PLLC

(57) ABSTRACT

An intraoral scanner includes a case having an opening part at one end thereof, a light source part at the other end of the case and configured to emit light, a first optical system including a first reflector to reflect the light emitted from the light source part and a second reflector disposed apart from the first reflector to reflect the light reflected by the first reflector toward the opening part, a second optical system in the opening part to reflect the light reflected from the first optical system toward a subject and reflect light reflected from the subject toward the second reflector, a third optical system adjacent to a back surface in the opposite direction of a reflective surface of the second reflector to reflect the light reflected from the second optical system, and an image sensor part to detect the light reflected from the third optical system.

10 Claims, 4 Drawing Sheets

(58) Field of Classification Search
CPC ............ A61B 1/00193; A61B 1/00194; A61B 1/0605; A61B 1/0615; A61B 1/247; A61B 5/0062; A61B 5/0088; A61C 9/0053; A61C 9/006; A61C 19/04
See application file for complete search history.

(56) References Cited

U.S. PATENT DOCUMENTS

| | | | | |
|---|---|---|---|---|
| 2013/0236850 | A1* | 9/2013 | Wu | G01B 11/24 433/29 |
| 2015/0223916 | A1* | 8/2015 | Kim | A61B 5/1079 433/29 |
| 2015/0288952 | A1* | 10/2015 | Popilka | A61B 5/4547 348/46 |
| 2015/0297324 | A1 | 10/2015 | Tchouprakov et al. | |
| 2016/0133112 | A1 | 5/2016 | Naoki et al. | |
| 2018/0080828 | A1* | 3/2018 | Fink | A61B 1/0625 |
| 2019/0247163 | A1 | 8/2019 | Wu et al. | |
| 2021/0045637 | A1 | 2/2021 | Chang et al. | |
| 2021/0093178 | A1 | 4/2021 | Long et al. | |
| 2023/0025243 | A1* | 1/2023 | Atiya | A61B 1/0638 |

FOREIGN PATENT DOCUMENTS

| | | | |
|---|---|---|---|
| JP | 2009-078133 | A | 4/2009 |
| JP | 2020-032058 | A | 3/2020 |
| KR | 10-1483216 | B1 | 1/2015 |
| KR | 10-1533341 | B1 | 7/2015 |
| KR | 10-2016-0133112 | A | 11/2016 |
| KR | 10-2021-0131642 | A | 11/2021 |
| WO | WO 2009/139110 | A1 | 11/2009 |
| WO | WO 2012/055347 | A1 | 5/2012 |
| WO | WO 2015/133824 | A1 | 9/2015 |

OTHER PUBLICATIONS

Notice of Allowance issued on Aug. 26, 2025 from Korean Patent Office in a counterpart Korean Patent Application No. 10-2024-0037236 (English translation is also submitted herewith.).

International Search Report for PCT/KR2022/020456 mailed on Mar. 17, 2023.

Office action issued on May 7, 2025 from Japan Intellectual Property Office in a counterpart Japanese Patent Application No. 2024-533150 (English translation is also submitted herewith. ).

Office action issued on Jul. 26, 2023 from Korean Patent Office in a counterpart Korean Patent Application No. 10-2021-0179478 (English translation is also submitted herewith.).

Notice of allowance issued on Febuary 21, 2024 from Korean Patent Office in a counterpart Korean Patent Application No. 10-2021-0179478 (English translation is also submitted herewith. ).

European Search Report For EP 22907966.0 issued on Sep. 1, 2025 from European patent office in a counterpart European patent application.

Examination Report issued on Apr. 8, 2026 from Intellectual Property India in a counterpart India Patent Application No. 202417040609.

Office action issued on Feb. 23, 2026 from UAE Ministry of Economy in a counterpart UAE Patent Application No. P2024-01521.

* cited by examiner

INTRAORAL SCANNER

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2022/020456 filed on Dec. 15, 2022, which claims priority to the benefit of Korean Patent Application No. 10-2021-0179478 filed on Dec. 15, 2021, in the Korean Intellectual Property Office, the entire contents of which are incorporated herein by reference.

BACKGROUND

1. Technical Field

The present disclosure relates to an intraoral scanner, and more particularly, to an intraoral scanner configured to obtain a 3D image of an oral cavity.

2. Background Art

Generally, an impression-taking procedure is performed in the process of diagnosis or treatment of a dental patient. Impression taking is a necessary clinical procedure in establishing a diagnosis and treatment plan for a patient by reflecting conditions of teeth and tissue in an oral cavity in an impression material. In recent years, with application of digital technology to dental clinic and lab processes, the number of cases of using a digital impression in which an oral cavity or an impression body is scanned and converted into digital data without using an impression material in impression taking has increased. In this way, with an increase in the importance of a digital impression in dental diagnosis and treatment, development of technology related to intraoral scanners has been actively carried out.

An intraoral scanner is a device or system inserted into an oral cavity of a dental patient to scan a 3D structure of teeth in a non-contact manner. Generally, recently developed intraoral scanners capture 2D image data of an oral cavity and perform 3D modeling of an oral cavity structure based on the 2D image data. The range of application of intraoral scanners having such functions has expanded among clinical applications, and the intraoral scanners may also be used in fabricating an implant, an orthodontic appliance, and the like in addition to being used in treatment for tooth restoration.

Meanwhile, impression accuracy is important for successful dental treatment. A digital impression using an intraoral scanner does not have a problem of deformation due to contraction, expansion, or the like of an impression material and thus has higher impression accuracy compared to a traditional impression-taking method. However, for an intraoral scanner to be continuously used as a tool for sophisticated dental treatment, there is a need to enhance scanning accuracy. Also, since an intraoral scanner is used by being inserted into an oral cavity of a dental patient in a non-contact manner, it is preferable for the intraoral scanner to have a structure that makes a patient feel comfortable during use of the intraoral scanner.

SUMMARY

Embodiments disclosed in the present specification provide an intraoral scanner having a plurality of optical systems disposed therein to have a structure suitable to be used by being inserted into an oral cavity of a dental patient in a non-contact manner.

One embodiment of the present disclosure provides an intraoral scanner including: a case having an opening part formed at one end thereof; a light source part disposed at the other end of the case and configured to emit light; a first optical system including a first reflector configured to reflect the light emitted from the light source part and a second reflector disposed apart from the first reflector and configured to reflect the light reflected by the first reflector toward the opening part; a second optical system disposed in the opening part and configured to reflect the light reflected from the first optical system toward a subject and reflect light reflected from the subject toward the second reflector; a third optical system disposed to be adjacent to a back surface in an opposite direction of a reflective surface of the second reflector and configured to reflect the light reflected from the second optical system; and an image sensor part configured to detect the light reflected from the third optical system.

According to one embodiment, the third optical system may include a fourth reflector configured to reflect the light reflected from the second optical system and a fifth reflector configured to reflect the light reflected by the fourth reflector toward the image sensor part.

According to one embodiment, the fourth reflector may include two reflective surfaces configured so that a dihedral angle between the reflective surfaces forms a minor angle, and the fifth reflector may include two reflective surfaces configured so that a dihedral angle between the reflective surfaces forms a major angle.

According to one embodiment, positions and directions of the two reflective surfaces of the fifth reflector may be set so that two images of the subject each reflected by the two reflective surfaces of the fifth reflector and detected by the image sensor part do not overlap with each other, and each of the images is entirely visible.

According to one embodiment, a gap may be formed at a central portion of the fourth reflector, light emitted from the fifth reflector may be configured to pass through the gap and reach the image sensor part, and the two reflective surfaces of the fifth reflector may be connected to each other at one side edge of each reflective surface.

According to one embodiment, the first optical system may be configured as a rhomboid prism including the first reflector and the second reflector.

According to one embodiment, the light source part may include a first light source part and a second light source part that emit light, the first light source part and the second light source part may be disposed at an upper portion and a lower portion, respectively, from the image sensor part, the first optical system may further include a third reflector disposed at a position symmetrical to the first reflector about the second reflector and configured to reflect the light emitted from the second light source part, the second reflector may include two reflective surfaces each configured to reflect one of the light reflected by the first reflector and the light reflected by the third reflector toward the opening part, and a dihedral angle between the reflective surfaces of the second reflector may be configured to form a major angle.

According to one embodiment, the light source part may be configured to emit patterned light or structured light.

According to one embodiment, the image sensor part may be configured to obtain two stereo images from an image of the light reflected from the third optical system.

According to one embodiment, the fourth reflector may include two pairs of reflective surfaces configured so that a dihedral angle between each pair of reflective surfaces forms a minor angle, the fifth reflector may include two reflective surfaces configured so that a dihedral angle between the reflective surfaces forms a major angle, positions and directions of the two reflective surfaces of the fifth reflector may be set so that four images of the subject each reflected by the two reflective surfaces of the fifth reflector and detected by the image sensor part do not overlap with each other, and each of the images is entirely visible, a gap may be formed at central portions of each pair of reflective surfaces of the fourth reflector, the light emitted from the fifth reflector may be configured to pass through the gap and reach the image sensor part, the two reflective surfaces of the fifth reflector may be connected to each other at one side edge of each reflective surface, and the image sensor part may be configured to obtain four stereo images from an image of the light reflected from the third optical system.

According to various embodiments of the present disclosure, since a driving part for angle adjustment of each of a plurality of optical systems disposed inside a case of an intraoral scanner is unnecessary, the optical systems can be densely arranged at optimal positions inside the case.

Also, according to various embodiments of the present disclosure, since it is possible to implement an intraoral scanner having a small volume by arranging a plurality of optical systems in a dense structure inside a case, during use of the intraoral scanner, it is not only easy to insert the intraoral scanner into an oral cavity of a dental patient but also easy to move or change a direction of the intraoral scanner in the oral cavity, and thus dental scanning can be precisely performed.

In addition, according to various embodiments of the present disclosure, since two or more stereo images can be obtained from images of light reflected from a plurality of optical systems with only a single image sensor part, manufacturing costs of an intraoral scanner can be reduced, and an internal configuration thereof can be further optimized.

Advantageous effects of the present disclosure are not limited to those mentioned above, and other unmentioned advantageous effects should be clearly understood by those of ordinary skill in the art from the claims below.

DETAILED DESCRIPTION

Figure 1:
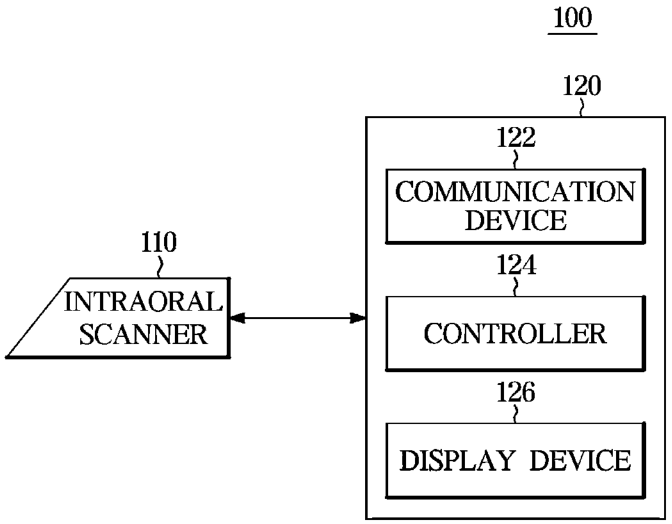
FIG. 1 is a block diagram illustrating a configuration in which an intraoral scanner according to one embodiment of the present disclosure is connected to an intraoral 3D modeling and visualization system.

Hereinafter, details for carrying out the present disclosure will be described in detail with reference to the accompanying drawings. However, in the description below, when there is concern about unnecessarily obscuring the gist of the present disclosure, detailed description of a widely known function or configuration will be omitted.

In the accompanying drawings, the same or corresponding components are denoted by the same reference numerals. Also, in the following description of embodiments, repeated description of the same or corresponding components may be omitted. However, omission of description of a certain component may not mean that the component is not included in a certain embodiment.

Terms used in the present disclosure will be briefly described, and embodiments disclosed herein will be described in detail. General terms that are currently widely used have been selected as terms used herein in consideration of functions in the present disclosure, but the terms may be changed according to an intention or practice of those of ordinary skill in the art, the advent of new technology, and the like. Also, in some cases, some terms may have been arbitrarily selected by the applicant, and in such cases, the meanings of the terms will be described in detail in the corresponding part of the description of the invention. Therefore, the terms used in the present disclosure should be defined based on the meanings of the terms and the content throughout the present disclosure, instead of being simply defined based on the names of the terms.

In the present disclosure, a singular expression includes a plural expression unless the context clearly indicates singularity. Also, a plural expression includes a singular expression unless the context clearly indicates plurality.

In the present disclosure, when a certain part is described as including a certain component, this indicates that the certain part may further include other components instead of excluding other components unless the context clearly indicates otherwise.

In the present disclosure, the upper part of a drawing may be referred to as "upper portion" or "upper side" of a configuration illustrated in the drawing, and the lower part of the drawing may be referred to as "lower portion" or "lower side" of the configuration. Also, a portion between the upper portion and the lower portion of the configuration illustrated in the drawing or a remaining portion excluding the upper portion and the lower portion may be referred to as "side portion" or "side surface" of the configuration. The relative terms such as "upper portion" and "upper side" may be used to describe the relationship between configurations illustrated in the drawings, and the present disclosure is not limited by the terms.

In the present disclosure, a direction toward an inner space of one structure may be referred to as "inner side," and a direction protruding to an open outer space may be referred to as "outer side." The relative terms such as "inner side" and "outer side" may be used to describe the relationship between configurations illustrated in the drawings, and the present disclosure is not limited by the terms.

In the present disclosure, the term "A and/or B" refers to A, B, or A and B.

In the present specification, when a certain part is described as being connected to another part, this not only includes a case in which the two parts are directly connected but also includes a case in which the two parts are connected with another configuration disposed therebetween.

Also, terms such as "module" or "part" used in the present disclosure refer to software or hardware components, and a "module" or "part" performs a certain role. However, the meaning of "module" or "part" is not limited to software or hardware. A "module" or "part" may be configured to be present in addressable storage media or configured to replay one or more processors. Therefore, as one example, a "module" or "part" may include at least one of components such as software components, object-oriented software components, class components, and task components, processes, functions, attributes, procedures, subroutines, program code segments, drivers, firmware, micro codes, circuits, data, databases, data structures, tables, arrays, or variables. The components and the "modules" or "parts" and functions provided therein may be combined into a smaller number of components and "modules" or "parts" or may be further separated into a larger number of components and "modules" or "parts."

Advantages and features of the embodiments disclosed herein and methods of achieving the same should become clear from embodiments described in detail below with reference to the accompanying drawings. However, the present disclosure is not limited to the embodiments disclosed below and may be implemented in various different forms. The present embodiments are only provided to make the present disclosure complete and completely inform those of ordinary skill in the art to which the present disclosure pertains of the scope of the invention.

FIG. 1 is a block diagram illustrating a configuration of an intraoral scanning system 100 in which an intraoral scanner 110 according to one embodiment of the present disclosure is connected to an intraoral 3D modeling and visualization server 120. As illustrated, the intraoral scanning system 100 may include the intraoral scanner 110 that can scan a 3D structure of an oral cavity of a dental patient and the intraoral 3D modeling and visualization server 120 connected to the intraoral scanner 110.

For example, the intraoral scanner 110 may be inserted into an oral cavity of a dental patient by a medical worker in a dental clinic to scan teeth in a non-contact manner and capture a plurality of pieces of 2D image data. Also, the intraoral scanner 110 may send the plurality of pieces of captured 2D image data to the 3D modeling and visualization server 120 or may perform 3D oral cavity structure modeling based on the 2D image data by itself.

The intraoral scanner 110 may be connected to the 3D modeling and visualization server 120 through a network configured to be able to communicate via a wire or wirelessly. Here, for example, according to an installation environment, the network may be configured with a wired network such as an electric connection line such as a copper cable, Ethernet, a wired home network (power line communication), a phone line communication device, and RS-serial communication, a wireless network such as a mobile network, a wireless local area network (WLAN), Wi-Fi, Bluetooth, and ZigBee, or a combination thereof.

The intraoral scanner 110 may transmit and receive information and/or data such as 2D image data and 3D oral cavity structure model data to and from the 3D modeling and visualization server 120. The intraoral scanner 110 and the 3D modeling and visualization server 120 may be configured to be physically separated as illustrated, but the present disclosure is not limited thereto. For example, the intraoral scanner 110 and the 3D modeling and visualization server 120 may be integrally configured in a single computing device.

The 3D modeling and visualization server 120 may perform 3D oral cavity structure modeling based on at least two pieces of 2D image data or stereo images obtained from the intraoral scanner 110. In order to perform such functions, the 3D modeling and visualization server 120 may correspond to a computing device including a processor that can perform image processing and 3D modeling (for example, a central processing unit (CPU), a graphics processing unit (GPU), an application processor (AP), a neutral processing unit (NPU), etc.) and a memory that can store 2D image data and 3D oral cavity structure model data. In one embodiment, the 3D modeling and visualization server 120 may include a communication device 122, a controller 124, and a display device 126 as illustrated. The communication device 122 may be configured to transmit and receive information and/or data to and from the intraoral scanner 110. Specifically, the communication device 122 may transmit a command signal of the controller 124 to the intraoral scanner 110 and may receive image information of a target oral cavity structure from the intraoral scanner 110.

The controller 124 may control the intraoral scanner 110 to capture an image of the target oral cavity structure. Specifically, the controller 124 may control at least one or more light source parts (for example, 220 in FIG. 2) installed inside the intraoral scanner 110 to emit light toward at least one of a plurality of optical systems. Also, the controller 124 may control an image sensor part (for example, 270 in FIG. 2) installed inside the intraoral scanner 110 to detect light reflected by at least one of the plurality of optical systems. The controller 124 may control the image sensor part to obtain at least two or more stereo images from an image of the detected light. The controller 124 may control the display device 126 to display the two or more stereo images received from the intraoral scanner 110. Alternatively or additionally, the controller 124 may control 3D oral cavity structure model data calculated based on the two or more stereo images to be visualized and displayed on the display device 126.

The display device 126 may display information and/or data received from the intraoral scanner 110 or the controller 124. In this case, data displayed on the display device 126 may include two stereo images or 3D oral cavity structure model images. In one embodiment, the display device 126 may include a display panel device such as a light emitting diode (LED) display, an organic light emitting diode (OLED) display, a liquid crystal display (LCD), or a touch display.

Figure 2:
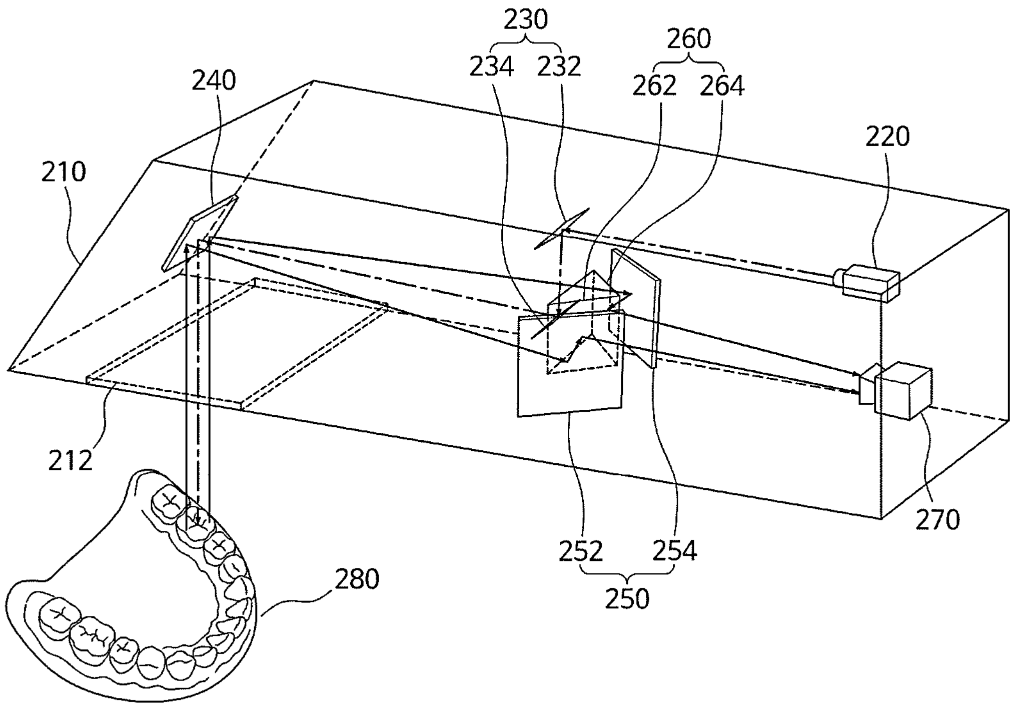
FIG. 2 is a see-through perspective view of the intraoral scanner according to one embodiment of the present disclosure.

FIG. 2 is a see-through perspective view of an intraoral scanner 200 according to one embodiment of the present disclosure. As illustrated in FIG. 2, the intraoral scanner 200 may include a case 210, a light source part 220, a first optical system 230, a second optical system 240, third optical systems 250 and 260, and an image sensor part 270.

The case 210 may be configured to form an exterior of the intraoral scanner 200 and accommodate the light source part 220, the first optical system 230, the second optical system 240, the third optical systems 250 and 260, and the image sensor part 270 therein. As illustrated in FIG. 2, the case 210 may have the shape of a trapezoidal box that substantially extends in any one longitudinal direction, but the present disclosure is not limited thereto. For example, the case 210 may have a rectangular parallelepiped shape, a cylindrical shape, a streamlined shape, or any other shape suitable for insertion into an oral cavity.

An opening part 212 may be formed at one end of the case 210. Specifically, the opening part 212 may include an opening formed at one end of the case 210. In this case, the opening of the opening part 212 may be configured to allow light generated or reflected inside the case 210 to be emitted to the outside and external light to be introduced into the case 210. In one embodiment, the opening part 212 may be configured to be positioned at the innermost side of an oral cavity when the intraoral scanner 200 is inserted into the oral cavity.

The light source part 220 may be configured to emit light toward the opening part 212, the first optical system 230, or the second optical system 240. In this case, light emitted from the light source part 220 may correspond to patterned light or structured light. The light may have a linear pattern, a dot pattern, or any other pattern. When patterned light is emitted to a subject 280 such as teeth in an oral cavity, deformation of the corresponding pattern may occur according to a 3D structure of a surface of the subject 280. Therefore, the 3D structure of the subject 280 may be identified and modeled based on the deformation of the pattern projected on the surface of the subject 280 or information on changes of positions of feature points.

The light source part 220 may be disposed at the other end of the case 210. Specifically, the light source part 220 may be disposed to be accommodated at the other end inside the case 210 that faces one end of the case 210 at which the opening part 212 or the second optical system 240 is formed. For example, the light source part 220 may be disposed to be fixed to an upper portion of the other end inside the case 210. In one embodiment, the light source part 220 may include a first light source part (for example, 822 in FIG. 8) and a second light source part (for example, 824 in FIG. 8). In this case, the first light source part and the second light source part may be disposed at the other end of the case together with the image sensor part 270 and may be disposed to be respectively fixed to the upper portion and lower portion of the other end inside the case 210 around the image sensor part. The configuration of the intraoral scanner 200 including the two light source parts will be described in detail below with reference to FIG. 8.

In one embodiment, the light source part 220 may be disposed at one side end of the case 210, but the present disclosure is not limited thereto. For example, the light source part 220 may be disposed at any intermediate point between one end and the other end of the case 210. That is, the light source part 220 may be disposed at any position inside the case 210 where it is easy for the light source part 220 to emit light toward the opening part 212, the first optical system 230, or the second optical system 240.

The first optical system 230 may be configured to reflect light emitted from the light source part 220 toward the second optical system 240 or the opening part 212. As illustrated in FIG. 2, the first optical system 230 may include a first reflector 232 and a second reflector 234. The first reflector 232 may be configured to reflect light emitted from the light source part 220 toward the second reflector 234. The first reflector 232 may be disposed to be fixed to an upper portion inside the case. Also, the second reflector 234 may be configured to reflect the light reflected by the first reflector 232 toward the second optical system 240 or the opening part 212. The second reflector 234 may be disposed to be spaced apart from the first reflector 232 and fixed to a central portion inside the case 210. That is, the light emitted from the light source part 220 may be reflected toward the second optical system 240 or the opening part 212 via the first reflector 232 and the second reflector 234 of the first optical system 230.

The second optical system 240 may be configured to reflect light emitted from the second reflector 234 of the first optical system 230 toward the subject 280 and reflect light reflected from the subject 280 toward the second reflector 234 or the third optical systems 250 and 260. The second optical system 240 may include at least one reflector. For example, the second optical system 240 may be at least one mirror. In one embodiment, the second optical system 240 may be disposed at the opening part 212 or around the opening part 212. For example, the second optical system 240 may be disposed to be fixed to an inner side surface of the opening part 212.

The third optical systems 250 and 260 may be configured to reflect light emitted from the second optical system 240. Specifically, the third optical systems 250 and 260 may reflect light emitted from the second optical system 240 toward the image sensor part 270. In this case, the third optical systems 250 and 260 may include one or more reflectors or mirrors configured to reflect light.

The third optical systems 250 and 260 may be disposed to be adjacent to a back surface in the opposite direction of a reflective surface of the second reflector 234 of the first optical system 230. Specifically, the light source part 220 and the second optical system 240 may be disposed to be fixed to both ends of the space inside the case 210, the first optical system 230 may be disposed at any position between the light source part 220 and the second optical system 240, and the third optical systems 250 and 260 may be disposed to be fixed to positions adjacent to the first optical system 230 in a direction in which the light source part 220 or the image sensor part 270 is positioned.

In one embodiment, the third optical systems 250 and 260 may include a fourth reflector 250 and a fifth reflector 260. The fourth reflector 250 may be configured to reflect light reflected from the second optical system 240 and emit the light toward the fifth reflector 260. In one embodiment, the fourth reflector 250 may include two reflective surfaces 252 and 254. The two reflective surfaces 252 and 254 may reflect the light reflected from the second optical system 240 toward the fifth reflector 260. Also, by a gap being formed between the two reflective surfaces 252 and 254, light reflected by the fourth reflector 250 and emitted from the fifth reflector 260 may pass through the gap and reach the image sensor part 270. Here, positions and directions of the two reflective surfaces 252 and 254 of the fourth reflector 250 may be set so that two images of the subject reflected by the two reflective surfaces 252 and 254 of the fourth reflector 250 and two reflective surfaces 262 and 264 of the fifth reflector 260 and detected by the image sensor part 270 do not overlap with each other. In one embodiment, the fourth reflector 250 may include two pairs of reflective surfaces, that is, four reflective surfaces (for example, 412, 414, 422, and 424 in FIG. 4). The configuration of the third optical systems 250 and 260 including the two pairs of reflective surfaces will be described in detail below with reference to FIG. 4.

The fifth reflector 260 may be configured to reflect light reflected from the fourth reflector 250 toward the image sensor part 270. In one embodiment, the fifth reflector 260 may include two reflective surfaces 262 and 264. The two reflective surfaces 262 and 264 may reflect the light reflected from the fourth reflector 250 toward the image sensor part 270. Light reflected from the fifth reflector 260 may pass through a gap formed at a central portion of the fourth reflector 250 and reach the image sensor part 270. Here, positions and directions of the two reflective surfaces 262 and 264 of the fifth reflector 260 may be set so that two images of the subject reflected by the two reflective surfaces 262 and 264 of the fifth reflector 260 and detected by the image sensor part 270 do not overlap with each other.

In one embodiment, the two reflective surfaces 262 and 264 of the fifth reflector 260 may be connected to each other through one side edge of each reflective surface. For example, the fifth reflector 260 may be a prism configured so that the two reflective surfaces 262 and 264 are adjacent to each other.

In one embodiment, each of the first optical system 230, the second optical system 240, and the third optical systems 250 and 260 may be disposed to be fixed to predetermined positions inside the case 210. In this case, a driving part for angle adjustment of the first optical system 230, the second optical system 240, or the third optical systems 250 and 260 may not be installed inside the case 210. In this way, since there is no need to arrange another electronic or mechanical component in an area inside the case where the first optical system 230, the second optical system 240, and the third optical systems 250 and 260 are disposed, the components inside the case may be densely arranged. Therefore, since it is possible to design an optimal structure of the case 210 from a dense structure of the first optical system 230, the second optical system 240, and the third optical systems 250 and 260, it is possible to freely perform a scanning operation in an oral cavity and implement the intraoral scanner 200 with a small volume.

In one embodiment, an angle formed between the two reflective surfaces 252 and 254 of the fourth reflector 250 may correspond to a minor angle, that is, an angle smaller than 180°, and an angle formed between the two reflective surfaces 262 and 264 of the fifth reflector 260 may correspond to a major angle, that is, an angle larger than 180°.

The image sensor part 270 may be configured to detect light reflected from the third optical systems 250 and 260. In one embodiment, the image sensor part 270 may be configured to obtain two stereo images from light reflected from the third optical systems 250 and 260. Specifically, the image sensor part 270 may simultaneously obtain two images of light reflected by the two reflective surfaces 262 and 264 of the fifth reflector 260 of the third optical systems 250 and 260. In this way, since the intraoral scanner 200 includes the third optical systems 250 and 260 having the plurality of reflective surfaces 252, 254, 262, and 264, two stereo images can be obtained with only the single image sensor part 270. The two stereo images obtained by the image sensor part 270 may be used in 3D oral cavity structure modeling performed by a processor afterwards. In one embodiment, the fourth reflector 250 may include two pairs of reflective surfaces, that is, four reflective surfaces (for example, 412, 414, 422, and 424 in FIG. 4), and the image sensor part 270 may be configured to obtain four stereo images from light reflected by the two reflective surfaces of the fifth reflector 260 of the third optical systems 250 and 260. The configuration in which the image sensor part 270 obtains four stereo images from the fifth reflector 260 including the two reflective surfaces will be described in detail below with reference to FIG. 5.

In one embodiment, the image sensor part 270 may be disposed at the other end of the case 210. Specifically, the image sensor part 270 may be disposed to be accommodated at the other end inside the case 210 to face the one end of the case 210 where the opening part 212 or the second optical system 240 is formed. For example, the image sensor part 270 may be disposed to be fixed to the lower portion inside the case 210 that is adjacent to the light source part 220.

Figure 3:
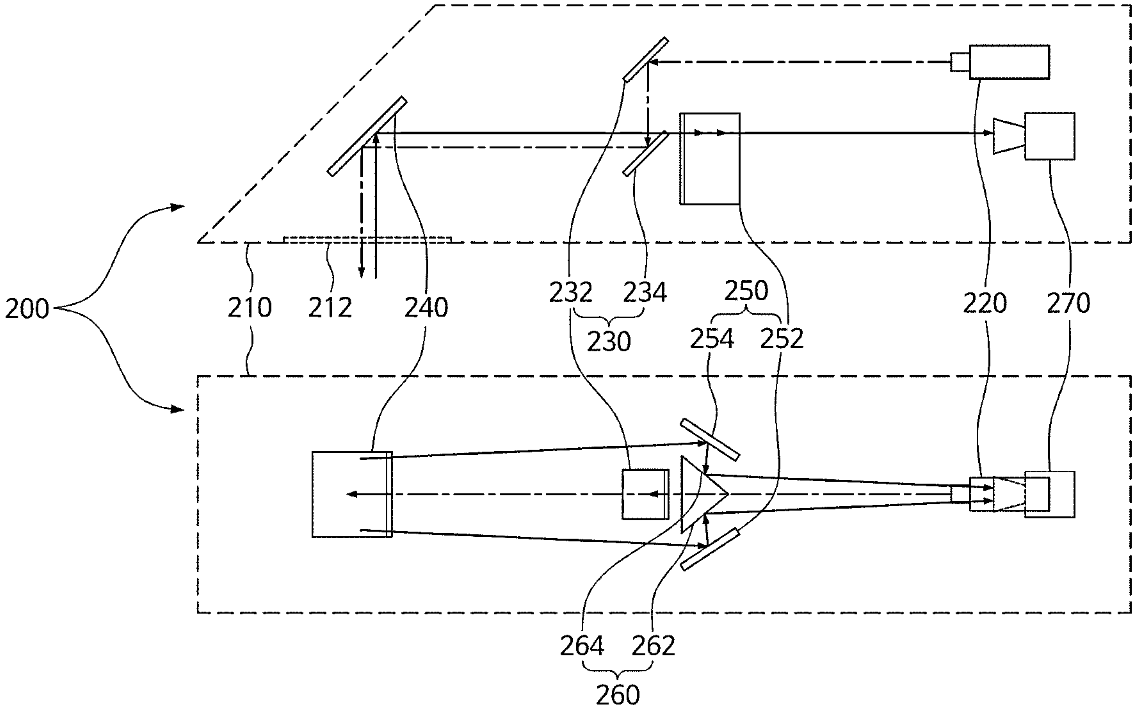
FIG. 3 shows a see-through lateral view and a see-through plan view of the intraoral scanner according to one embodiment of the present disclosure.

FIG. 3 shows a see-through lateral view and a see-through plan view of the intraoral scanner 200 according to one embodiment of the present disclosure. Configurations of FIG. 3 that overlap with FIG. 2 will be briefly described based on the embodiment illustrated in FIG. 3. In one embodiment, light may be emitted from the light source part 220 and may be reflected toward the second optical system 240 by the first reflector 232 and the second reflector 234 of the first optical system 230. Light reflected from the second reflector 234 may be reflected toward the subject positioned outside the case 210 by the second optical system 240. In this case, light may pass through an opening formed at one side of the opening part 212. Light reflected from the subject may be reflected toward the fourth reflector 250 of the third optical systems by the second optical system 240. Light reflected by the fourth reflector 250 may be reflected toward the image sensor part 270 by the fifth reflector 260.

In this case, the light source part 220 and the second optical system 240 may be disposed to be fixed to both ends of the space inside the case 210. Also, the first optical system 230 disposed at any position between the light source part 220 and the second optical system 240 may be disposed in an area that does not interfere with a path along which light that is reflected from the subject and reflected toward the third optical systems 250 and 260 by the second optical system 240 passes, that is, a blind area. That is, the first optical system 230 may be disposed in an area that does not overlap with a portion of light reflected from the subject that is incident on the third optical systems 250 and 260 (for example, an area adjacent to back surfaces in the opposite direction of the two reflective surfaces 262 and 264 of the fifth reflector 260). In this way, by each of the first optical system 230 and the third optical systems 250 and 260 being appropriately disposed in a blind area instead of a valid optical path while an optical path of the first optical system 230 and optical paths of the third optical systems 250 and 260 do not interfere with each other, the components inside the case may be more densely arranged.

Figure 4:
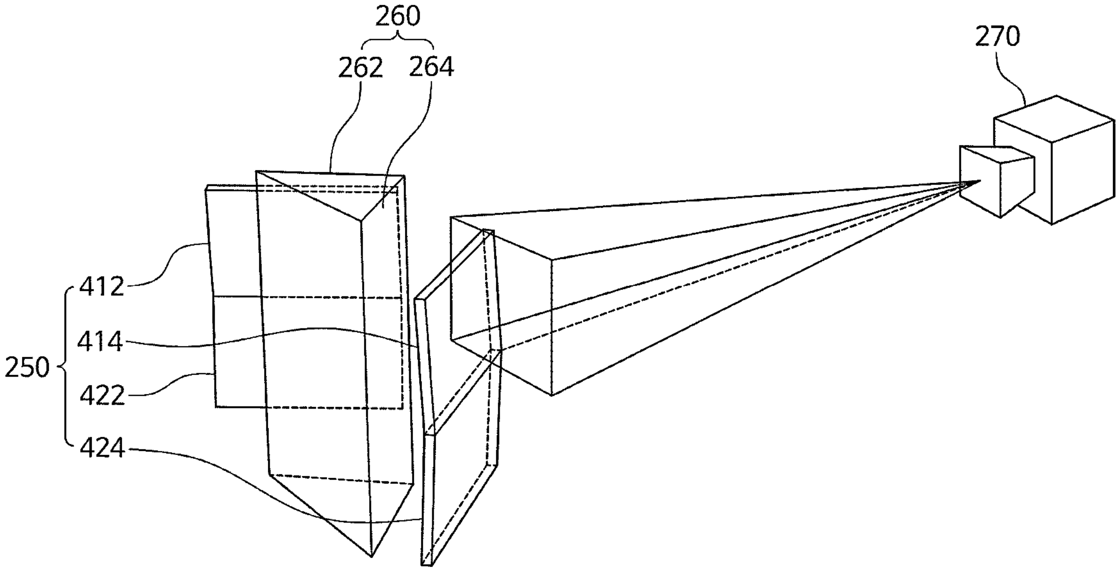
FIG. 4 is a see-through perspective view of a third optical system of the intraoral scanner according to one embodiment of the present disclosure.

FIG. 4 is a see-through perspective view of the third optical systems 250 and 260 of the intraoral scanner according to one embodiment of the present disclosure. Configurations of FIG. 4 that overlap with FIG. 2 will be briefly described based on the embodiment illustrated in FIG. 4. In one embodiment, the third optical systems 250 and 260 may include the fourth reflector 250 configured to reflect light reflected from the second optical system and the fifth reflector 260 configured to reflect light reflected by the fourth reflector 250 toward the image sensor part 270.

In one embodiment, the fourth reflector 250 may include two pairs of reflective surfaces, that is, four reflective surfaces 412, 414, 422, and 424, configured so that a dihedral angle between each pair of reflective surfaces is a minor angle. In this case, the first pair of reflective surfaces 412 and 414 may be configured so that a dihedral angle between the reflective surfaces is a minor angle. Similarly, the second pair of reflective surfaces 422 and 424 may be configured so that a dihedral angle between the reflective surfaces is a minor angle. Also, the fifth reflector 260 may include the two reflective surfaces 262 and 264 configured so that a dihedral angle between the reflective surfaces is a major angle. In this case, the two reflective surfaces 262 and 264 may be configured to be connected to each other through one side edge of each reflective surface. Here, the positions and directions of the four reflective surfaces 412, 414, 422, and 424 of the fourth reflector 250 may be set so that two images of the subject each reflected by the four reflective surfaces 412, 414, 422, and 424 of the fourth reflector 250 and the two reflective surfaces 262 and 264 of the fifth reflector 260 and detected by the image sensor part do not overlap with each other. Also, the positions and directions of the two reflective surfaces 262 and 264 of the fifth reflector 260 may be set so that two images of the subject each reflected by the two reflective surfaces 262 and 264 of the fifth reflector 260 and detected by the image sensor part 270 do not overlap with each other.

According to such a configuration, the image sensor part 270 may obtain four stereo images from light reflected by the two reflective surfaces of the fifth reflector 260 of the third optical systems 250 and 260. A result of the image sensor part 270 obtaining the four stereo images from the fifth reflector 260 including the two reflective surfaces will be described in detail below with reference to FIG. 5.

Figure 5:
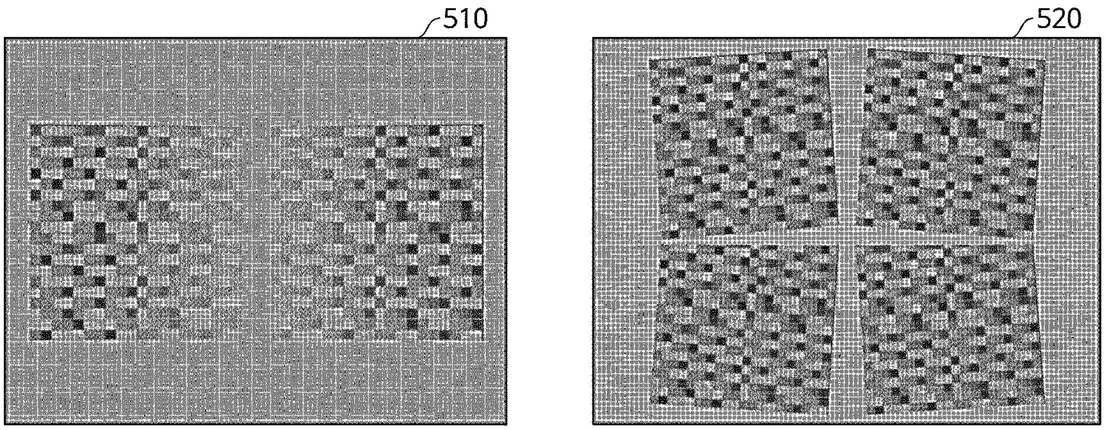
FIG. 5 is a view illustrating examples of stereo images obtained according to one embodiment of the present disclosure.

FIG. 5 is a view illustrating examples of stereo images 510 and 520 obtained according to one embodiment of the present disclosure. The image sensor part (for example, 270 in FIG. 2) may be configured to detect light reflected from the third optical systems (for example, 250 and 260 in FIG. 2). In one embodiment, the image sensor part may be configured to obtain two stereo images 510 from light reflected from the third optical systems. Specifically, the image sensor part may simultaneously obtain two stereo images reflected by the two reflective surfaces (for example, 262 and 264 in FIG. 2) of the fifth reflector (for example, 260 in FIG. 2) of the third optical systems. The processor may extract depth data based on the two stereo images obtained in this way and may perform 3D modeling of an oral cavity structure, which is a subject, based on the depth data.

In one embodiment, the image sensor part may be configured to obtain four stereo images 520 from light reflected from the third optical systems. Specifically, the image sensor part may simultaneously obtain four stereo images reflected by the four reflective surfaces (for example, 412, 414, 422, and 424 in FIG. 4) of the fourth reflector (for example, 250 in FIG. 4) of the third optical systems and the two reflective surfaces (for example, 262 and 264 in FIG. 4) of the fifth reflector (for example, 260 in FIG. 4). The processor may extract depth data based on the four stereo images obtained in this way and may perform 3D modeling of an oral cavity structure, which is a subject, based on the depth data. In this case, for example, by performing 3D modeling of an oral cavity structure, which is a subject, based on data obtained by comparison analysis of differences between the lower left image of the four stereo images 520 and the other three stereo images, a more sophisticated 3D model can be obtained.

Figure 6:
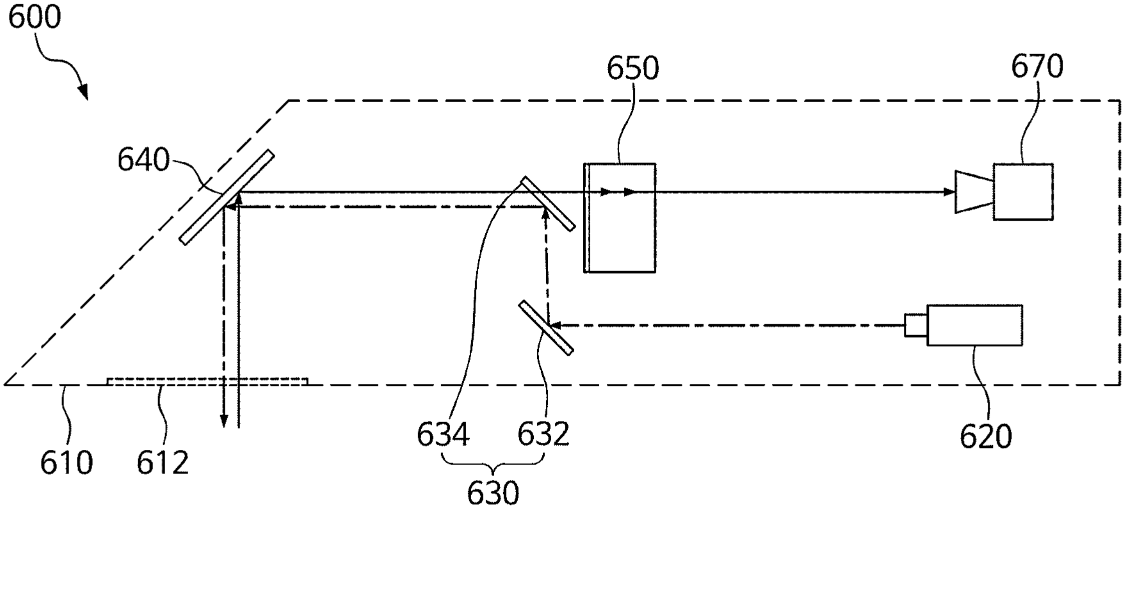
FIG. 6 is a see-through lateral view of an intraoral scanner according to another embodiment of the present disclosure.

FIG. 6 is a see-through lateral view of an intraoral scanner 600 according to another embodiment of the present disclosure. Configurations of FIG. 6 that overlap with FIG. 2 will be briefly described based on the embodiment illustrated in FIG. 6. As illustrated in FIG. 6, a light source part 620 may be configured to emit light toward an opening part 612. The light source part 620 may be disposed to be accommodated at the other end inside a case 610 that faces one end of the case 610 at which the opening part 612 or a second optical system 640 is formed. For example, the light source part 620 may be disposed to be fixed to a lower portion of the other end inside the case 610.

In one embodiment, a first optical system 630 may be configured to, through a first reflector 632 and a second reflector 634, reflect light emitted from the light source part 620 toward the opening part 612 or the second optical system 640. Specifically, the first reflector 632 disposed to be fixed to a lower portion inside the case 610 may be configured to reflect light emitted from the light source part 620 toward the second reflector 634. Also, the second reflector 634 may be configured to reflect the light reflected by the first reflector 632 toward the opening part 612 or the second optical system 640. The second reflector 634 and the first reflector 632 may be disposed to be spaced apart from each other and fixed to a central portion inside the case 610.

Light reflected from the second reflector 634 may be reflected toward a subject by the second optical system 640. In this case, the light may pass through an opening formed at one side of the opening part 612. Light reflected from the subject may be reflected again toward a third optical system 650 by the second optical system 640. Light reflected by the third optical system 650 may be reflected toward an image sensor part 670. Here, the third optical system 650 may include the same configuration as the third optical systems 250 and 260 illustrated in FIG. 2.

As illustrated, the light source part 620 and the second optical system 640 may be disposed to be fixed to both ends of the space inside the case 610. Also, the first optical system 630 disposed at any position between the light source part 620 and the second optical system 640 may be disposed in an area that does not interfere with a path along which light that is reflected from the subject and reflected toward the third optical system 650 by the second optical system 640 passes, that is, a blind area.

Figure 7:
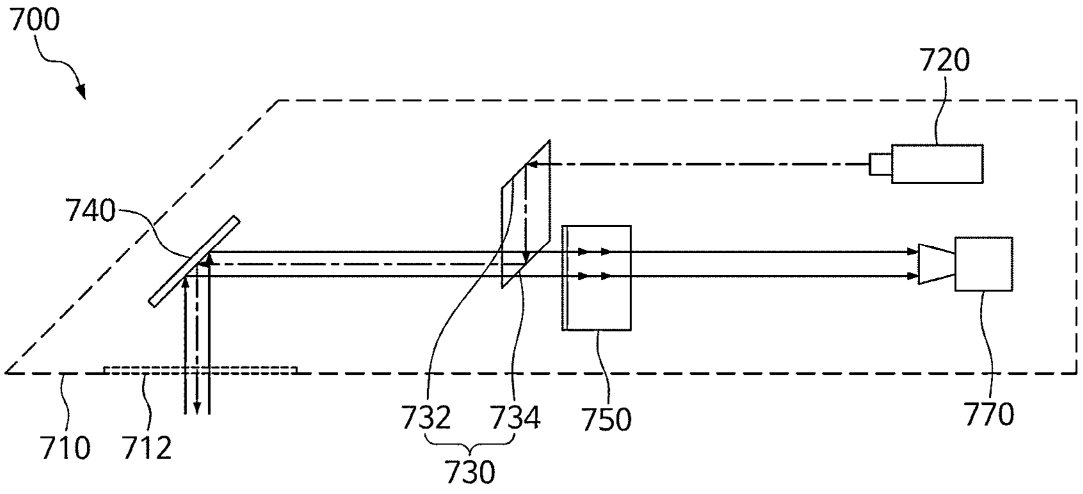
FIG. 7 is a see-through lateral view of an intraoral scanner according to still another embodiment of the present disclosure.

FIG. 7 is a see-through lateral view of an intraoral scanner 700 according to still another embodiment of the present disclosure. Configurations of FIG. 7 that overlap with FIG. 2 will be briefly described based on the embodiment illustrated in FIG. 7. As illustrated in FIG. 7, a light source part 720 may be configured to emit light toward an opening part 712 or a first optical system 730. The light source part 720 may be disposed to be accommodated at the other end inside a case 710 that faces one end of the case 710 at which the opening part 712 or a second optical system 740 is formed. For example, the light source part 720 may be disposed to be fixed to an upper portion of the other end inside the case 710.

In one embodiment, the first optical system 730 may include a rhomboid prism including a first reflector 732 and a second reflector 734. In this case, light emitted from the light source part 720 may be reflected toward the opening part 712 through the first reflector 732 and the second reflector 734 of the prism. That is, the first reflector 732 of the prism may be configured to reflect the light emitted from the light source part 720 toward the second reflector 734. Also, the second reflector 734 may be configured to reflect the light reflected by the first reflector 732 toward the opening part 712 or the second optical system 740. That is, the light emitted from the light source part 720 may be reflected toward the second optical system 740 or the opening part 712 via the rhomboid prism of the first optical system 730.

Light reflected from the second reflector 734 of the rhomboid prism may be reflected toward a subject by the second optical system 740. In this case, light may pass through an opening formed at one side of the opening part 712. Light reflected from the subject may be reflected again toward a third optical system 750 by the second optical system 740. Light reflected by the third optical system 750 may be reflected toward an image sensor part 770. Here, the third optical system 750 may include the same configuration as the third optical systems 250 and 260 illustrated in FIG. 2.

As illustrated, the light source part 720 and the second optical system 740 may be disposed to be fixed to both ends of the space inside the case 710. Also, the rhomboid prism, which is the first optical system 730 disposed at any position between the light source part 720 and the second optical system 740, may be disposed in an area that does not interfere with a path along which light that is reflected from the subject and reflected toward the third optical system 750 by the second optical system 740 passes, that is, a blind area.

Figure 8:
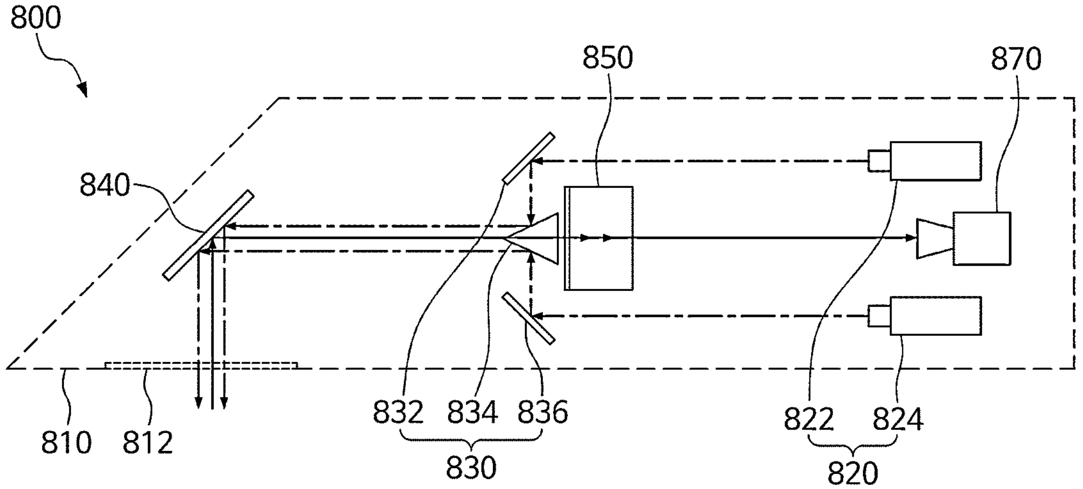
FIG. 8 is a see-through lateral view of an intraoral scanner according to yet another embodiment of the present disclosure.

FIG. 8 is a see-through lateral view of an intraoral scanner 800 according to yet another embodiment of the present disclosure. Configurations of FIG. 8 that overlap with FIG. 2 will be briefly described based on the embodiment illustrated in FIG. 8. As illustrated in FIG. 8, a light source part 820 may be configured to emit light toward an opening part 812 or a first optical system 830. The light source part 820 may include a first light source part 822 and a second light source part 824. Any one ray of light among rays of light emitted from the first light source part 822 and the second light source part 824 may correspond to patterned light or structured light, and another ray of light may correspond to normal light without a pattern. The first light source part 822 and the second light source part 824 may be configured to alternately emit light at predetermined time intervals. Also, the first light source part 822 and the second light source part 824 may be disposed together with an image sensor part 870 at the other end of a case 810 that faces one end of the case at which the opening part 812 is installed and may be disposed to be respectively fixed to an upper portion and a lower portion of the other end inside the case 810 while being symmetrical to each other about the image sensor part 870.

In one embodiment, the first optical system 830 may be configured to reflect light emitted from the light source part 820 toward the opening part 812 through a first reflector 832, a second reflector 834, and a third reflector 836. That is, the first reflector 832 and the third reflector 836 may be configured to reflect light emitted from the light source part 820 toward the second reflector 834. The first reflector 832 may be disposed to be fixed to an upper portion inside the case, and the third reflector 836 may be disposed to be fixed to a lower portion inside the case. Also, the second reflector 834 may include two reflective surfaces each configured to reflect one of the light reflected by the first reflector 832 and the light reflected by the third reflector 836 toward the opening part 812 or a second optical system 840. In this case, a dihedral angle between the reflective surfaces of the second reflector 834 may be configured to form a major angle. The second reflector 834 may be disposed to be spaced apart from the first reflector 832 and the third reflector 836 and fixed to a central portion inside the case 810. That is, light emitted from the light source part 820 may be reflected toward the opening part 812 or the second optical system 840 via the first reflector 832, the third reflector 836, and the second reflector 834 of the first optical system 830.

Light reflected from the second reflector 834 may be reflected toward a subject by the second optical system 840. In this case, light may pass through an opening formed at one side of the opening part 812. Light reflected from the subject may be reflected again toward a third optical system 850 by the second optical system 840. Light reflected by the third optical system 850 may be reflected toward the image sensor part 870. Here, the third optical system 850 may include the same configuration as the third optical systems 250 and 260 illustrated in FIG. 2.

As illustrated, the light source part 820 and the second optical system 840 may be disposed to be fixed to both ends of the space inside the case 810. Also, the first optical system 830 disposed at any position between the light source part 820 and the second optical system 840 may be disposed in an area that does not interfere with a path along which light that is reflected from the subject and reflected toward the third optical system 850 by the second optical system 840 passes, that is, a blind area. That is, the first optical system 830 may be disposed in an area that does not overlap with a portion of light reflected from the subject that is incident on the third optical system 850 (for example, an area adjacent to back surfaces in the opposite direction of the two reflective surfaces 262 and 264 of the fifth reflector 260). In this way, by each of the first optical system 830 and the third optical system 850 being appropriately disposed in a blind area instead of a valid optical path while an optical path of the first optical system 830 and an optical path of the third optical systems 850 do not interfere with each other, the components inside the case may be more densely arranged.

The exemplary embodiments of the present invention which have been described above are only disclosed for illustrative purposes. Those of ordinary skill in the art to which the present invention pertains may make various modifications, changes, and additions within the spirit and scope of the present invention, and such modifications, changes, and additions also belong to the scope of the claims.

Since various substitutions, alterations, and changes may be made within the scope not departing from the technical spirit of the present invention by those of ordinary skill in the art to which the present invention pertains, the present invention is not limited by the embodiments described above or the accompanying drawings.

What is claimed is:

1. An intraoral scanner comprising:

a case having an opening part formed at one end thereof;

a light source part disposed at the other end of the case and configured to emit light;

a first optical system including a first reflector configured to reflect the light emitted from the light source part and a second reflector disposed apart from the first reflector and configured to reflect the light reflected by the first reflector toward the opening part;

a second optical system disposed in the opening part and configured to reflect the light reflected from the first optical system toward a subject and reflect light reflected from the subject toward the second reflector;

a third optical system disposed to be adjacent to a back surface in an opposite direction of a reflective surface of the second reflector and configured to reflect the light reflected from the second optical system; and an image sensor part configured to detect the light reflected from the third optical system.

2. The intraoral scanner of claim 1, wherein the third optical system includes:

a fourth reflector configured to reflect the light reflected from the second optical system; and a fifth reflector configured to reflect the light reflected by the fourth reflector toward the image sensor part.

3. The intraoral scanner of claim 2, wherein:

the fourth reflector includes two reflective surfaces configured so that a dihedral angle between the reflective surfaces forms a minor angle; and the fifth reflector includes two reflective surfaces configured so that a dihedral angle between the reflective surfaces forms a major angle.

4. The intraoral scanner of claim 2, wherein positions and directions of the two reflective surfaces of the fifth reflector are set so that two images of the subject each reflected by the two reflective surfaces of the fifth reflector and detected by the image sensor part do not overlap with each other, and each of the images is entirely visible.

5. The intraoral scanner of claim 4, wherein:

a gap is formed at a central portion of the fourth reflector, and light reflected by the fifth reflector is configured to pass through the gap and reach the image sensor part; and the two reflective surfaces of the fifth reflector are connected to each other at one side edge of each reflective surface.

6. The intraoral scanner of claim 1, wherein the first optical system is configured as a rhomboid prism including the first reflector and the second reflector.

7. The intraoral scanner of claim 1, wherein:

the light source part includes a first light source part and a second light source part that emit light, and the first light source part and the second light source part are disposed at an upper portion and a lower portion, respectively, from the image sensor part;

the first optical system further includes a third reflector disposed at a position symmetrical to the first reflector about the second reflector and configured to reflect the light emitted from the second light source part;

the second reflector includes two reflective surfaces each configured to reflect one of the light reflected by the first reflector and the light reflected by the third reflector toward the opening part; and a dihedral angle between the reflective surfaces of the second reflector is configured to form a major angle.

8. The intraoral scanner of claim 1, wherein the light source part is configured to emit patterned light or structured light.

9. The intraoral scanner of claim 1, wherein the image sensor part is configured to obtain two stereo images from an image of the light reflected from the third optical system.

10. The intraoral scanner of claim 2, wherein:

the fourth reflector includes two pairs of reflective surfaces configured so that a dihedral angle between each pair of reflective surfaces forms a minor angle;

the fifth reflector includes two reflective surfaces configured so that a dihedral angle between the reflective surfaces forms a major angle;

positions and directions of the four reflective surfaces of the fourth reflector are set so that four images of the subject each reflected by the four reflective surfaces of the fourth reflector and the two reflective surfaces of the fifth reflector and detected by the image sensor part do not overlap with each other, and each of the images is entirely visible;

positions and directions of the two reflective surfaces of the fifth reflector are set so that four images of the subject each reflected by the two reflective surfaces of the fifth reflector and detected by the image sensor part do not overlap with each other, and each of the images is entirely visible;

a gap is formed at central portions of each pair of reflective surfaces of the fourth reflector, and the light emitted from the fifth reflector is configured to pass through the gap and reach the image sensor part;

the two reflective surfaces of the fifth reflector are connected to each other at one side edge of each reflective surface; and the image sensor part is configured to obtain four stereo images from an image of the light reflected from the third optical system.

* * * * *